US009192303B2

(12) United States Patent
Gulsen et al.

(10) Patent No.: US 9,192,303 B2
(45) Date of Patent: Nov. 24, 2015

(54) TEMPERATURE-MODULATED FLUORESCENCE TOMOGRAPHY

(71) Applicant: The Regents of the University of California, Oakland, CA (US)

(72) Inventors: Gultekin Gulsen, Irvine, CA (US); Yuting Lin, Mission Viejo, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 13/719,157

(22) Filed: Dec. 18, 2012

(65) Prior Publication Data

US 2013/0189188 A1 Jul. 25, 2013

Related U.S. Application Data

(60) Provisional application No. 61/577,624, filed on Dec. 19, 2011.

(51) Int. Cl.
*A61B 5/05* (2006.01)
*A61B 5/00* (2006.01)

(52) U.S. Cl.
CPC ............. *A61B 5/0071* (2013.01); *A61B 5/0073* (2013.01); *A61B 5/0097* (2013.01)

(58) Field of Classification Search
CPC .... A61B 5/007; A61B 5/0073; A61B 5/1455; A61B 5/4312; A61B 2562/02
See application file for complete search history.

(56) References Cited

U.S. PATENT DOCUMENTS

| 5,784,162 | A | 7/1998 | Cabib et al. |
| 6,443,898 | B1 * | 9/2002 | Unger et al. ................. 600/458 |
| 7,599,732 | B2 * | 10/2009 | Sevick-Muraca et al. .... 600/476 |
| 7,620,445 | B2 | 11/2009 | Tsujita |
| 2011/0319765 | A1 * | 12/2011 | Gertner et al. ............... 600/453 |
| 2013/0184591 | A1 * | 7/2013 | Tesar ........................... 600/473 |

OTHER PUBLICATIONS

Ale, et al. "Imaging Performance of a Hybrid X-ray Computed Tomography-Fluorescence Molecular Tomography System Using Priors," *Medical Physics*, vol. 37, No. 5, pp. 1976-1986, May 2010.
Chen, et al. "Thermo/pH-Responsive and Reversible NIR Fluorescent Probes for Optical Molecular Imaging," *Biomedical Optics*, OSA Technical Digest, JMA 105, 3 pages, 2010.
Davis, et al. "Magnetic Resonance-Coupled Fluorescence Tomography Scanner for Molecular Imaging of Tissue," *Review of Scientific Instruments*, vol. 79, pp. 064302-1-064302-10, 2008.
Escobedo, et al. "NIR Dyes for Bioimaging Applications," *Current Opinion in Chemical Biology*, vol. 14, No. 1, Author Manuscript, Feb. 2010, 11 pages.
"Fluorescence Imaging, Principles and Methods," Amersham Biosciences 2002, 166 pages.
Gruber, et al. "High-Frequency Ultrasound-Guided Fluorescence Tomography of Protoporphyrin IX in Subcutaneous Tumors," *Biomedical Optics*, OSA Technical Digest, BMB5, 2010, 3 pages.

(Continued)

*Primary Examiner* — Joel Lamprecht
(74) *Attorney, Agent, or Firm* — Knobbe Martens Olson & Bear LLP (57) ABSTRACT

Aspects of the disclosure relate to fluorescence imaging, and more particularly to the use of temperature modulation in a tissue site with a modulator such as high intensity focused ultrasound to modulate the emission signal emitted by temperature-sensitive optical fluorescence reporters.

20 Claims, 6 Drawing Sheets

(56) References Cited

OTHER PUBLICATIONS

Kepshire, et al. "A Microcomputed Tomography Guided Fluorescence Tomography System for Small Animal Molecular Imaging," *Review of Scientific Instruments*, vol. 80, pp. 043701-1-043701-10, 2009.

Kherlopian, et al. "A Review of Imaging Techniques for Systems Biology," downloaded from http://www.biomedcentral.com, originally published in *BMC Systems Biology*, vol. 2, No. 74, Aug. 12, 2008, 18 pages.

Kim, et al. "Evaluation of Temperature-Sensitive, Indocyanine Green-Encapsulating Micelles for Noninvasive Near-Infrared Tumor Imaging," *Pharmaceutical Research*, vol. 27, No. 9, pp. 1900-1913, 2010.

Klibanov, "Ligand-Carrying Gas-Filled Microbubbles: Ultrasound Contrast Agents for Targeted Molecular Imaging," *Bioconjugate Chemistry*, vol. 16, No. 1, pp. 9-17, 2005.

Kobayashi, et al. "Fluorescence Tomography in Turbid Media Based on Acousto-Optic Modulation Imaging," *Applied Physics Letters*, vol. 89. pp. 181102-1-181102-3, 2006.

Leblond, et al. "Pre-Clinical Whole-Body Fluorescence Imaging: Review of Instruments, Methods and Applications," *Journal of Photochemistry and Photobiology B: Biology*, vol. 98, No. 1, pp. 77-94, 2010.

Li, et al. "Simultaneous Molecular and Hypoxia Imagining of Brain Tumors In Vivo Using Spectroscopic Photoacoustic Tomography," *Proceedings of the IEEE*, vol. 96, No. 3, pp. 481-489, Mar. 2008.

Lin, et al. "Quantitative Fluorescence Tomography Using a Trimodality System: In Vivo Validation," *Journal of Biomedical Optics*, vol. 15, No. 4, pp. 040503-1-040503-3, Jul./Aug. 2010.

Lin, et al. Quantitative Fluorescence Tomography Using a Combined Tri-Modality FT/DOT/XCT System *Optics Express*, vol. 18, No. 8, pp. 7835-7850, Apr. 12, 2010.

Lin, et al. "Temperature-modulated Fluorescence Tomography Based on Both Concentration and Lifetime Contrast," *Journal of Biomedical Optics*, vol. 17, No. 5, pp. 56007-1-056007-4, May 2012.

Ling, et al. "Towards Multidimensional Radiotherapy (MD-CRT): Biological Imaging and Biological Conformity," *International Journal of Radiation Oncology\*Biology\*Physics*, vol. 47, No. 3, pp. 551-560, 2000.

Lin, et al. "Temperature-modulated Fluorescence Tomography in a Turbid Media," *Applied Physics Letters*, vol. 100 073702-1-073702-4, 2012.

Ma, et al. "Multispectral Optoacoustic Tomography (MSOT) Scanner for Whole-Body Small Animal Imaging," *Optics Express*, vol. 17, No. 24, pp. 121414-21426, Nov. 23, 2009.

Ntziachristos, Going Deeper than Microscopy: The Optical Imaging Frontier in Biology, *Nature Methods*, vol. 7, No. 8, pp. 603-614, Aug. 2010.

Ranzansky, et al. "Multispectral Opto-Acoustic Tomography of Deep-Seated Fluorescent Proteins In Vivo," *Nature Photonics*, vol. 3, No. 7, pp. 412-417, Jul. 2009.

Schutt, "Ultrasound-Modulated Fluorescent Contrast Agent for Optical Imaging Through Turbid Media," *Proceedings of SPIE*, vol. 8165 (1), 81650B, Sep. 8, 2011.

Takalkar, et al. "Binding and Detachment Dynamics of Microbubbles Targeted to P-Selectin Under Controlled Shear Flow," *Journal of Controlled Release*, vol. 96, pp. 473-482, 2004.

Wang, "Prospects of Photoacoustic Tomography" *Medical Physics*, vol. 36, No. 12, pp. 5758-5767, Dec. 2008.

Wang, et al. "Temperature-modulated Bioluminescence Tomography," *Optics Express*, vol. 14, No. 17, pp. 7852-7871, Aug. 21, 2006.

Wu, et al. *Biomedical Optics: Principles and Imaging*, 1$^{st}$ Edition, Wiley-Interscience, New Jersey, Chapters 12 and 13, 2007.

Xu, et al. "Photoacoustic Imaging in Biomedicine," *Review of Scientific Instruments*, vol. 77, pp. 041101-1-041101-22, 2006.

Yuan, "Ultrasound-Modulated Fluorescence Based on a Fluorophore-Quencher-Labeled Microbubble System" *Journal of Biomedical Optics*, vol. 14, No. 2, 024043, Apr. 17, 2009.

Yuan, et al. "Microbubble-Enhanced Ultrasound-Modulated Fluorescence in a Turbid Medium," *Applied Physics Letter*, vol. 95, No. 18, pp. 181113-1-181113-3, 2009.

\* cited by examiner

TEMPERATURE-MODULATED FLUORESCENCE TOMOGRAPHY

STATEMENT REGARDING FEDERALLY SPONSORED R&D

The invention was made with government support under grants CA120175 and EB008716 from the National Institutes of Health. The government has certain rights in the invention.

BACKGROUND OF THE INVENTION

1. Field of the Invention

Aspects disclosed herein relate to fluorescence based reporter imaging, and more particularly to the use of temperature modulation in a scattering medium with high intensity focused ultrasound or any other form of radiation to modulate the optical signal emitted by temperature-sensitive optical reporters.

2. Description of the Related Art

High scattering in biological tissues does not permit optical imaging of fluorescence in thick tissue with high resolution. As one of the optical imaging techniques, fluorescence tomography (FT) utilizes laser light to excite the fluorescence sources located deep in a medium. Once excited, these sources relax to their ground state in nanoseconds by emitting lower energy photons. While propagating towards the surface of the medium, these photons are subject to a vast amount of scattering events along the way. This makes the FT inverse problem exceptionally difficult, and the FT inverse problem is defined as the problem of recovering the fluorescence source distribution from the measured light intensities on the tissue surface. Accordingly, the resolution and quantitative accuracy of the reconstructed images are very low[2].

In the past, there has been extensive effort to improve the resolution of fluorescence tomography (FT). One approach is to integrate FT with other anatomic imaging modalities such as x-ray, MRI and ultrasound[11-16]. However, the weakness of this approach is that it does not perform well if the fluorescent target cannot be localized in the anatomical image. The low modulation efficiency and extremely low signal to noise ratio make the implementation of ultrasound modulation of fluorescence signals difficult[3,4].

Meanwhile, an intriguing combination of optical and ultrasound techniques has led to the development of photo-acoustic tomography (PAT) that can provide the optical absorption maps with much higher resolution (~1 mm) and a depth penetration of three to five centimeters[1,17,18]. PAT has been successfully applied to recover spatially resolved tissue intrinsic contrast maps with very high resolution. Although it can also provide distribution of exogenous contrast agents using multiple-wavelength measurements, PAT is inherently sensitive to absorption and detects differential increase in absorption due to molecular probes compared to background absorption[19-21].

One proposed solution to this problem is to induce periodic displacement of scattering particles and variation of the refractive index in the medium using a focused ultrasound field. Using this approach and scanning the focused ultrasound field over the probed medium, ultrasound modulated fluorescence tomography (UMFT) can enhance the resolution[3,4]. However, only a small fraction of the photons that travels through the focused ultrasound column can be modulated at a time. The low modulation efficiency and extremely low signal to noise ratio (SNR) are the two main factors that make its implementation difficult.

Another proposed solution is to use micro-bubbles surface-loaded with self quenching fluorophores to enhance the contrast of UMFT[5,6]. However, some disadvantages of such microbubbles are their instability, low circulation residence times, low binding efficiency to the area of interest especially in the fast-flow conditions and possible side effects of their destruction during the imaging session[7,8].

SUMMARY OF THE INVENTION

A temperature-modulated fluorescence tomography imaging system is disclosed. The imaging system comprises: an excitation light source configured to generate excitation light; an optical reporter configured to absorb excitation light and emit an optical signal; a temperature-modulating energy source configured to modulate the temperature of the optical reporter; and a detector configured to detect the optical signal after temperature modulation of the optical reporter. In some embodiments, the excitation light source is selected from a laser, a light emitting diode, and a UV light.

The optical reporter may comprise a temperature-sensitive fluorescence contrast agent. The temperature-sensitive fluorescence contrast agent may comprise ICG loaded nanocapsules.

The temperature-modulating energy source may be configured to deliver high intensity focused ultrasound energy to the optical reporter. In other embodiments, the temperature-modulating energy source may be configured to deliver microwave energy to the optical reporter. In other embodiments, the temperature-modulating energy source may be configured to deliver radio frequency energy to the optical reporter. In other embodiments, the temperature-modulating energy source may be configured to deliver near-infrared energy to the optical reporter.

A temperature-modulated fluorescence tomography imaging method is disclosed in other embodiments. The imaging method comprises: administering an optical reporter to a site for imaging, wherein the optical reporter is configured to absorb excitation light and emit an optical signal; irradiating the site with excitation light; delivering sufficient temperature-modulating energy to the site to modulate the temperature of the optical reporter; and detecting the optical signal emitted by the optical reporter.

In some embodiments of the imaging system and method, the optical reporter may comprise a temperature-sensitive fluorescence contrast agent. The temperature-sensitive fluorescence contrast agent may comprise ICG loaded nanocapsules.

In some embodiments, the temperature-modulating energy is high intensity focused ultrasound energy. In other embodiments, the temperature-modulating energy is microwave energy. In other embodiments, the temperature-modulating energy is radio frequency energy. In other embodiments, the temperature-modulating energy is near-infrared energy.

In some embodiments, a fluorescence intensity and/or a fluorescence lifetime of the optical signal is determined.

In some embodiments, the imaging method further comprises rendering a quantitatively accurate image using a reconstruction algorithm.

BRIEF DESCRIPTION OF THE DRAWINGS

FIG. 1 is a schematic diagram of one embodiment of a Temperature-Modulated Tomography ("TM-FT") system. A HIFU transducer is driven by a combination of a signal generator and an RF power amplifier. Using an xyz translational stage, it is scanned over the probed medium that is simultaneously irradiated with modulated laser light. The intensity variations are detected using a photomultiplier tube and then measured by a Network Analyzer.

FIG. 3(a) shows the experimental set-up of one embodiment of the TM-FT system. The imaging system 10 comprises, for example, an excitation light source 11, optical fibers 12 to transmit the excitation light to the probed medium and detect fluorescence emission signal changes due to the temperature variation, a temperature-modulating energy source configured to modulate the temperature of the optical reporter, for example high-intensity focused ultrasound 14, a phantom containing the optical reporter 16, and a detector 18 configured to detect the optical signal after temperature modulation of the optical reporter. FIG. 3(b) is a diagram of the transducer zoom in view. During the HIFU scan, a localized temperature increase on the focal spot (~1.5 mm size) is generated. As a result, the measured fluorescence signal only changes when the focal spot is on the fluorescence source.

FIG. 4 shows the results that uses one embodiment of the TM-FT system to image a phantom.

DETAILED DESCRIPTION

This disclosure relates generally to systems and methods for imaging, and more particularly to temperature-modulated fluorescence tomography ("TM-FT"). TM-FT involves using an optical reporter that is administered to or deployed at a site of interest for imaging. The optical reporter is configured to absorb light energy and emit an optical (e.g., fluorescent) signal. The intensity and/or lifetime of the optical signal are temperature-dependent. In some embodiments, the optical reporter includes a photoactive component, e.g., a fluorophore, in association with a thermally responsive component, e.g., polymeric nanoparticles or nanocapsules. In such embodiments, the fluorophore is configured to absorb excitation light at one wavelength and emit light (or fluoresce) at another wavelength, and the polymeric nanoparticles or nanocapsules are configured to absorb energy and generate heat—thereby modulating the temperature of the fluorophore. The fluorophore may be encapsulated within a nanocapsule or otherwise associated with nanoparticles. Besides the aforementioned optical reporter, the disclosed temperature-modulated fluorescence tomography system and methods also include an excitation light source, for example, a laser or light emitting diode, capable of irradiating the optical reporters at the site of interest, thereby causing the optical reporter to generate an emission light signal. The disclosed temperature-modulated fluorescence tomography system and methods also include an energy source, e.g., a high intensive focused ultrasound transducer, configured to deliver sufficient energy to modulate the temperature at the site—thereby modulating the emission signal of the optical reporter.

Excitation light (or radiation) sources can include broad-wavelength sources, such as ultraviolet and xenon arc lamps, line sources such as lasers, and light emitting diodes. Laser sources may include argon ion lasers, helium neon lasers, Neodymium:Yttrium Aluminum Garnet solid-state lasers, and diode lasers. The excitation light may be collimated or filtered or directed with optical lenses, mirrors, galvanometers, or moving-head scanners. Excitation light sources may be selected to match the absorption spectrum of the optical reporter.

The optical reporter may emit a fluorescence signal.

Polymeric nanoparticles or nanocapsules are useful tools for applications in imaging. Polymeric hydrogel nanoparticles with thermal responsiveness are particularly attractive as imaging tools. Furthermore, the surface of the nanocapsules can be modified using ligands and/or other functional moieties to achieve target specific and/or facilitated intracellular delivery of the nanocapsule contents. Nanocapsules can be loaded with a variety of dyes, including, but not limited to, for example, indocyanine green (ICG) and other cyanines (such as, but not limited to, tricarbocyanines, pyrrolopyrrole cyanines, benzo[c,d]indolium-derived cyanines, functional cyanines, hydrocyanines, and iodoacetamide-functionalized cyanines), porphyrins, phthalocyanines, squaraine, boron-dipyrromethane analogs, benzo[c]heterocycles, fluorophores (such as, but not limited to fluorescein and Cy3 fluorochrome), xanthenes, and IR800.

The temperature-modulating energy source configured to modulate the temperature of the optical reporter can include one or more energy characteristic, for example, one or more of a waveform, frequency, amplitude, or duration. The temperature modulator configured to modulate the temperature of the optical reporters includes one or more of ultrasonic energy (e.g., HIFU), acoustic energy, or any other form of electromagnetic energy, microwave energy, radio frequency, near-infrared energy, or thermal energy.

A variety of detectors can be used to detect the emission energy from the optical reporters for this invention. Detector configurations may include lenses, mirrors, and filters. Detectors may also include amplifiers of the signal. Emission signal detection may employ a photodiode detector or array of photodiode detectors, photomultiplier tube(s) or a charge-coupled device, any of which convert light energy into electrical current or voltage. Other detectors may include Avalanche Photodiode or hybrid Avalanche Photodiode & solid-state photo multiplier tubes.

In one embodiment, TM-FT may utilize focused ultrasound to heat the medium, typically only a couple of degrees Celsius, but with a high degree of spatial resolution. One element of this TM-FT embodiment is the recently emerged temperature-sensitive fluorescence contrast agents such as but not limited to ICG loaded pluronic nanocapsules, which may be used in accordance with aspects of TM-FT. For example, Yongping et. al. and Kim et. al. both demonstrated similar nanocapsules earlier in 2010[9,10]. The quantum efficiency of these nanocapsules is shown to be sensitive to temperature. For example, when heated from 22 to 40° C., the fluorescence light intensity emitted by these nanocapsules increases two-to four-fold, and was shown to be reversible. Generally, any temperature sensitive fluorescence contrast agent that works in any temperature range can be utilized with this technique. This TM-FT technique leverages the temperature dependence of such contrast agents to overcome the spatial resolution limitation of conventional FT by using temperature modulation/tagging.

In certain embodiments of the TM-FT technique, the medium is irradiated by both excitation light and a high intensity focused ultrasound (HIFU) wave. The HIFU beam is scanned over the site in either step-and-shoot or continuous-scan mode. The crucial benefit of HIFU is that the temperature of the medium is modulated with very high spatial resolution (~1.5 mm) due to the absorption of acoustic power in the ultrasound focal zone. Local temperature increases may affect the fluorescence intensity, quantum efficiency and fluorescence lifetime of the sensitive fluorescence agents present within the HIFU focal zone. As a result, the emitted fluorescence light intensity and the lifetime of the fluorescence may both exhibit a substantial change. The difference in the detected fluorescence signal following the HIFU temperature modulation can render the position of these nanocapsules with high spatial resolution. Furthermore, this can be achieved without using a complex reconstruction algorithm as in the case for conventional FT.

To illustrate one embodiment of the TM-FT process for high resolution fluorescence tomography, the light propagation and heat transfer is modeled using a finite element method framework. With diffusion approximation as the light propagation model in turbid medium, the TM-FT process may be formulated with the following equations. Eq. 1 and Eq. 2 describe conditions before and after the application of the HIFU beam to obtain selective localized heating in the medium, respectively:

$$-\nabla \cdot (D\nabla \phi_o^m) + \mu_a \phi_o^m = \eta(T_o)\mu_{af}\phi^x \quad (1); \text{ and}$$

$$-\nabla \cdot (D\nabla \phi_i^m) + \mu_a \phi_i^m = \theta(T_i)\delta(\vec{x} - \vec{x}_i)\mu_{af}\phi^x, \, 1 \leq i \leq N \quad (2).$$

with the diffusion coefficient D,
the absorption coefficient $\mu_a$,
the photon density at excitation ($\phi^x$),
emission wavelength ($\phi^m$), and
fluorescence absorption coefficient $\mu_{af}$.

Assuming that the scanning area consists of discrete locations [$\vec{x}_i$, i≤N]. The ideal focused heating at $\vec{x}_i$ corresponds to a delta function in Eq. 2, which can be approximated by a compactly supported and fast decaying function in practice. Let $d_i = \phi^m_i - \phi^m_o$ and $c = \eta(T_i) - \eta(T_o)$, we have:

$$-\nabla \cdot (D\nabla d_i) + \mu_a d_i = c\delta(\vec{x} - \vec{x}_i)\mu_{af}(x_i)\phi^x, 1 \leq i \leq N \quad (3)$$

The difference measurement $d_i$, only has values when the scanning step $\vec{x}_i$ is nonzero for $\mu_{af}(\vec{x}_i)$. Therefore, when the HIFU scans over the probed medium, the TM-FT could produce high resolution fluorescence images even without any reconstruction process. As a simpler alternative approach, TM-FT raw images can be used as priori information to guide and constrain conventional FT reconstruction algorithm to obtain quantitatively accurate fluorescence images.

WORKING EXAMPLES

Figure 1:
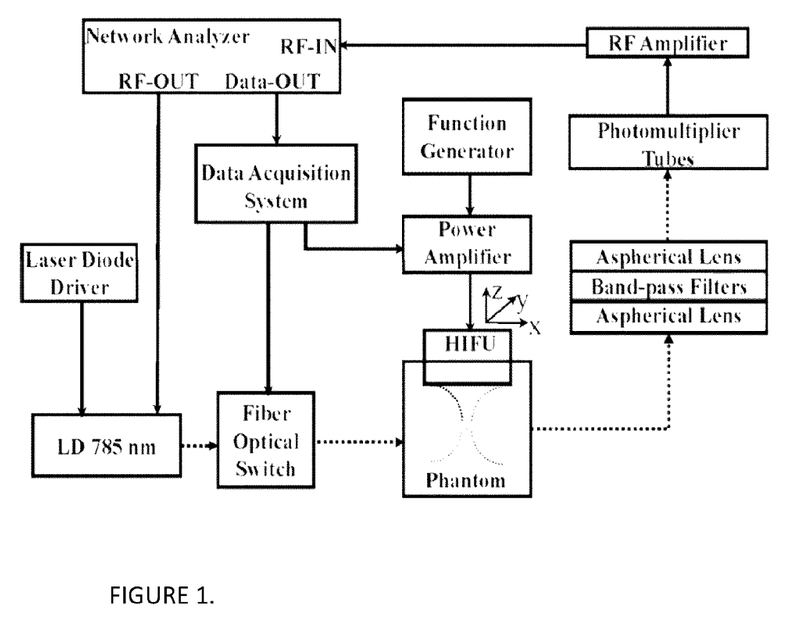

Experimental studies were carried out to demonstrate that the TM-FT could penetrate several centimeters thick scattering tissue, yet still at ultrasound resolution (sub-millimeter). The schematic diagram of the system is shown in FIG. 1. A 785 nm laser diode (80 mW, Thorlabs, Newton, N.J.) was used for fluorescence excitation. This laser wavelength was chosen due to high absorption of ICG, the fluorescence contrast agent used in this particular nanocapsule. Any wavelength can be used depending on the absorption spectrum of the particular fluorescent agent used in the nanocapsule. Near-infrared (NIR) wavelength range (600-1100 nm) would be especially suitable for in vivo imaging due to low absorption of tissue in this range. A network analyzer (Agilent Technologies, Palo Alto, Calif.) not only provided the RF modulation for the laser-diode but also measured the amplitude of the detected signal at the same time. A photomultiplier tube (PMT) (R7400U-20 Hamamatsu, Japan) was used to detect fluorescence signal due to its high sensitivity. A 65 dB RF amplifier was used to amplify the output signal of the PMT. To effectively eliminate the excitation light, two cascaded band-pass filters (830 nm, MK Photonics, Albuquerque, N. Mex.) were used on the detection site. A collimation system based on two aspherical lenses (Newport Corporation, Calif.) was designed to achieve maximum filtering efficiency. The HIFU transducer (H102, Sonic Concepts, Inc. Wash.) with a center frequency of 1.1 MHz was mounted on a xyz translational stage and used to generate focused hot spot. The lateral full width half maximum (FWHM) of the focal spot was 1.33 mm. The transducer was driven by a sinusoidal signal generated by a functional generator (PTS 500, Programmed Test Sources, Inc. Wash.) and amplified by a power amplifier (200L, Amplifier Research, Inc. Pa.).

Figure 2:
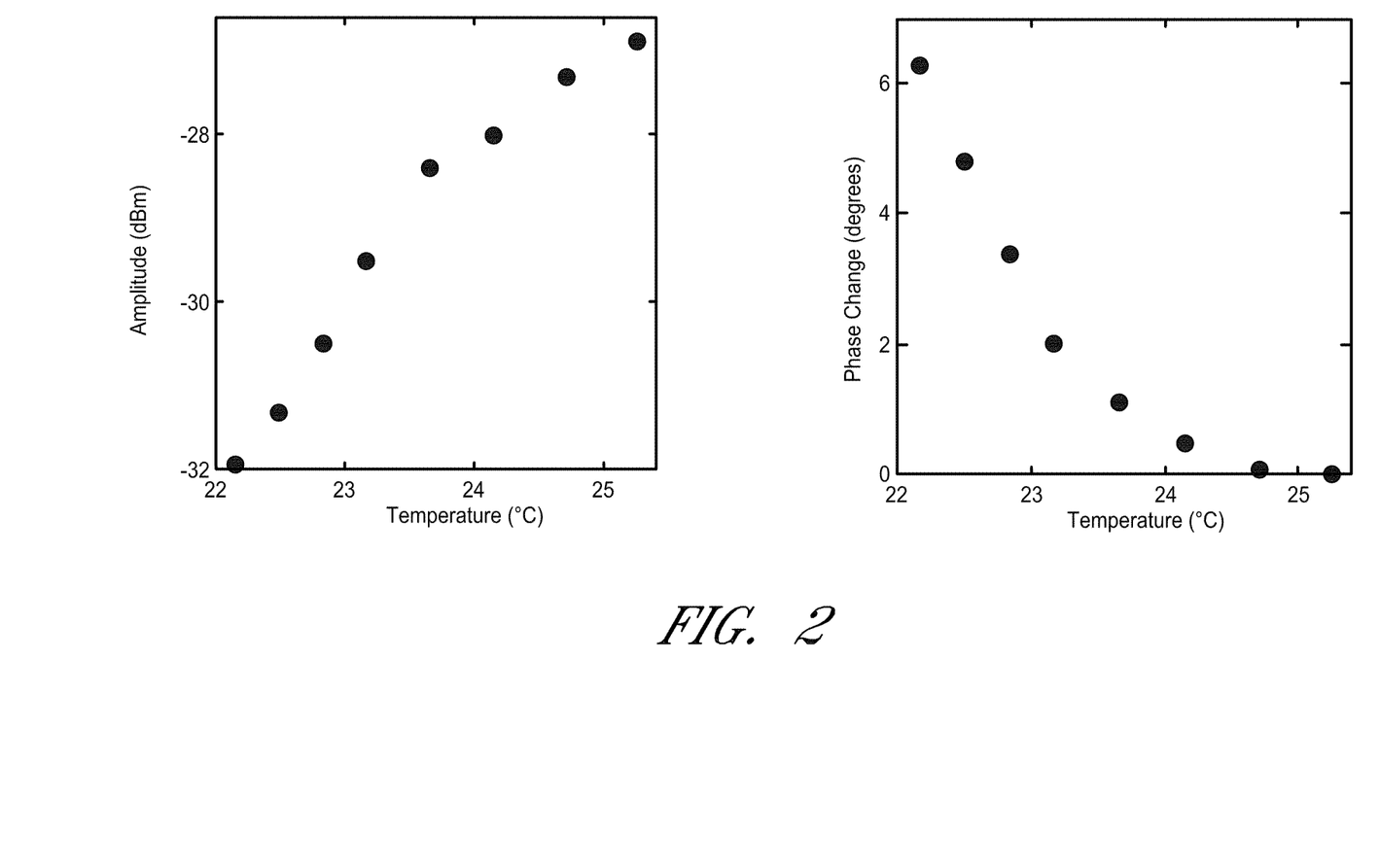
FIG. 2 is a graph showing the temperature response of the fluorescence contrast agent Pluronic ICG. The amplitude and phase of the recorded signals are given in (a) and (b), respectively. The temperature is measured using a fiber optical temperature sensor.
Figure 3A:
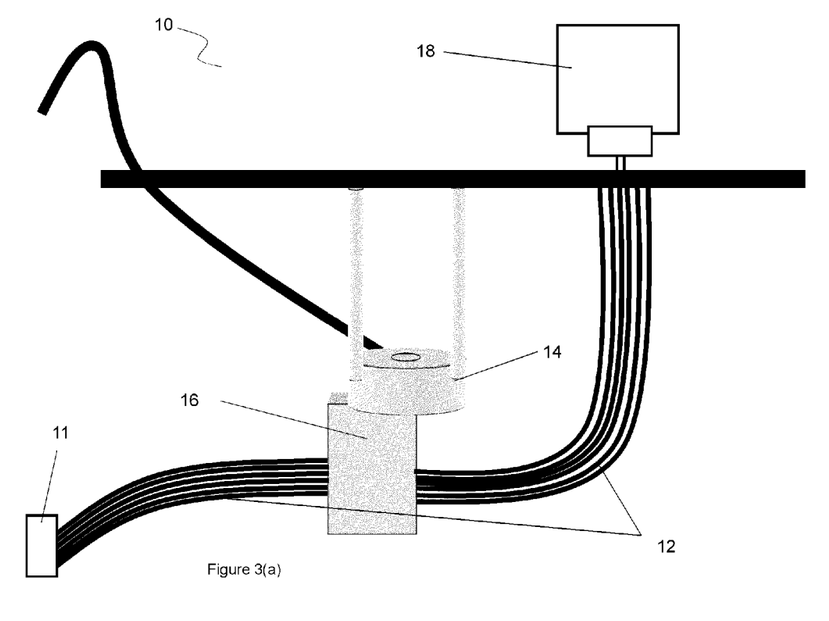
Figure 3B:
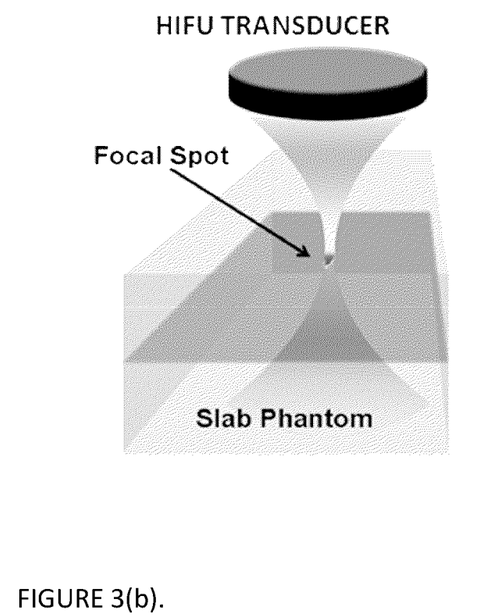

The experimental set up that was used is shown in FIG. 3, 10. A 4 cm×10 cm×10 cm slab gel phantom made from agarose was immersed in a water/intralipid tank 16. The HIFU transducer 14 was mounted on an xyz translational stage and placed on top of the phantom. The transducer was scanned laterally in both x and y directions. Optical fibers 12 were used to transmit the excitation light from the excitation light source 11 to the probed medium and detect fluorescence emission signal changes due to the temperature variation. The measurement at each scan position was averaged four times, which yields two seconds acquisition time for each point. In order to know the point spread function (PSF) of the temperature profile generated by the HIFU, an fiber-optic temperature sensor was inserted in an agarose phantom and the temperature change was recorded when the HIFU was scanned through a 5 mm×5 mm area with 0.5 mm steps in step-and-shoot mode. Computer controlled translation stages were used to scan HIFU transducer in x, y, and z directions. This PSF can be used to improve the resolution of the TM-FT images further using deconvolution approach. If fast scanning time is required, however, HIFU can be continuously scanned over the area while the HIFU power was applied in continuous-wave or pulsed mode. For 3D measurements two HIFU transducers working in orthogonal directions can be used. The temperature response of the fluorescence contrast agents called "ThermoDots" is shown in FIG. 2. As shown, both amplitude and phase of the measured signal changes indicating a change in both quantum efficiency and lifetime of the fluorescence agent. The profile across the sensor tip shows the temperature increase as a function of x-position of the HIFU scan step. The FWHM of the heating spot size was 1.8 mm that corresponds to point spread function of the system, which in turn becomes the spatial resolution limitation for this set-up.

Figure 4A:
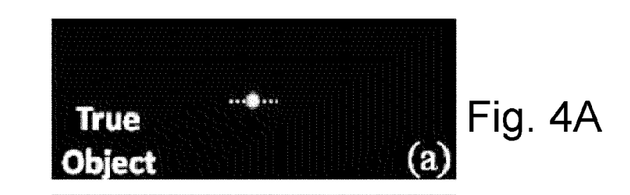
FIG. 4(a) is the true size and position of the inclusion.
Figure 4B:
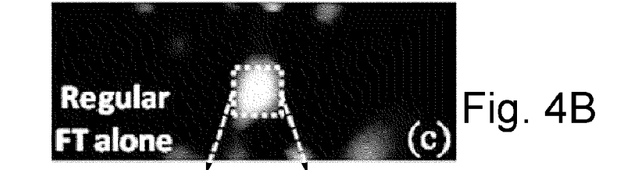
FIG. 4(b) is the experimental set-up used for both conventional and TM FT systems for this specific experiment.
Figure 4C:
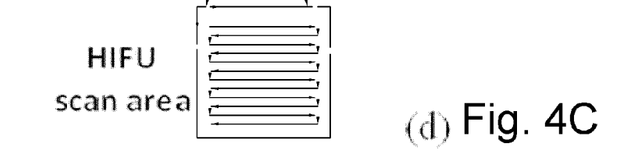
FIG. 4(c) is the reconstructed fluorescence map using conventional fluorescence tomography. The scanning area is represented by the dashed lines.
Figure 4D:
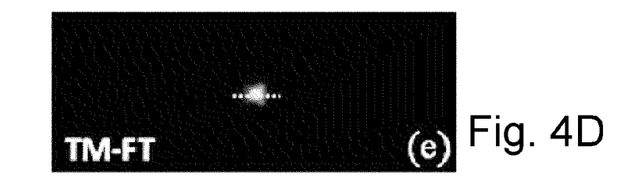
FIG. 4(d) shows the HIFU transducer being scanned through an 8 mm×8 mm area while the fluorescence measurements are taken.
Figures 4E, 4F:
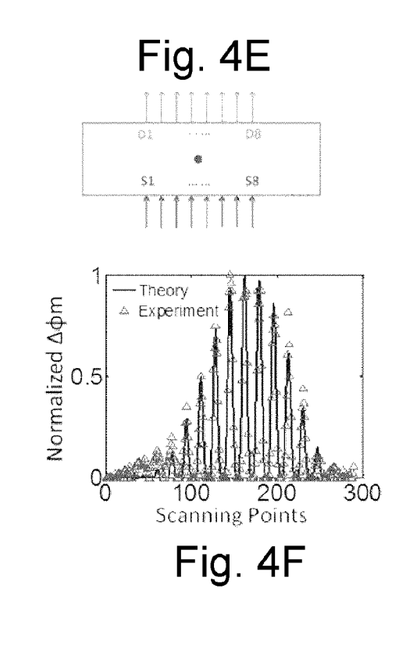
FIG. 4(e) shows the reconstructed fluorescence map using temperature modulated fluorescence tomography. As seen from the figure, TM-FT provides superior resolution and quantitative accuracy.
FIG. 4(f) shows a comparison of the experimentally measured fluorescence intensity change and those predicted by the theoretical model. The theoretical prediction is shown in blue circle lines, while the experimental data is plotted in red triangle lines.
Figure 4G:
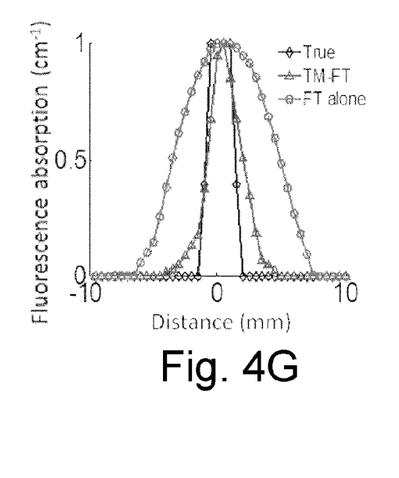
FIG. 4(g) shows the normalized profiles plot across the fluorescence source shows that the size of the fluorescence source is accurately recovered as well as the agent concentration.

A 3 mm fluorescence inclusion filled with Pluronic-ICG (Innosense Inc) was embedded in the middle of the phantom. Intralipid (0.5%) and Indian Ink are added as scatterer and absorber, making the scatter and absorption coefficient of the phantom 0.005 mm$^{-1}$ and 0.6 mm$^{-1}$, respectively. The actual size, position and concentration of the inclusion are shown in FIG. 4(a). First conventional FT measurements are acquired. FIG. 4(b) is the experimental set-up used for both conventional and TM FT systems for this specific experiment. FIG. 4(c) shows the conventional FT reconstruction. A region of interest is determined from this image (ROI$_{TM}$) and then the HIFU is scanned through it (8 mm×8 mm area) with 0.5 mm steps, FIG. 4(c). For each step, the HIFU power is turned on for two seconds, and the resulting temperature in the inclusion is kept below 40° C. The fluorescence signal variation is mapped to each scanning position and significant change is observed only when the HIFU hot spot is scanned through the fluorescence object (FIG. 4(d)), resulting in a much improved spatial resolution. FIG. 4(e) shows the reconstructed fluorescence map using temperature modulated fluorescence tomography. As seen from the figure, TM-FT provides superior resolution and quantitative accuracy. The comparison of the experimentally measured fluorescence intensity change and those predicted by the theoretical model is shown in FIG. 4(f). Excellent agreement between the theory and experiment was obtained for this case. There was some deviation observed, which is likely attributed to the contribution of residual heating from the previous scanning step. The profiles plot across the fluorescence source for the true object and the object recovered from the TM-FT is shown in FIG. 4(g). The FWHM of the recovered object size from the TM-FT is 3.2 mm, which is close to 3.0 mm true object size.

Figure 5A:
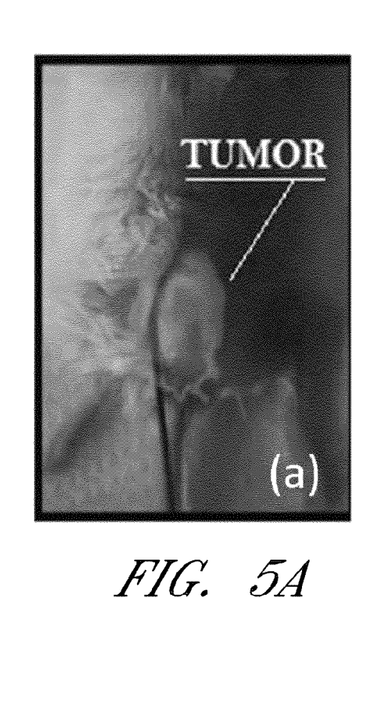
FIG. 5(a) shows fluorescence image of a temperature-sensitive contrast agent injected into a rat bearing R3220 AC breast cancer tumor model.
Figure 5B:
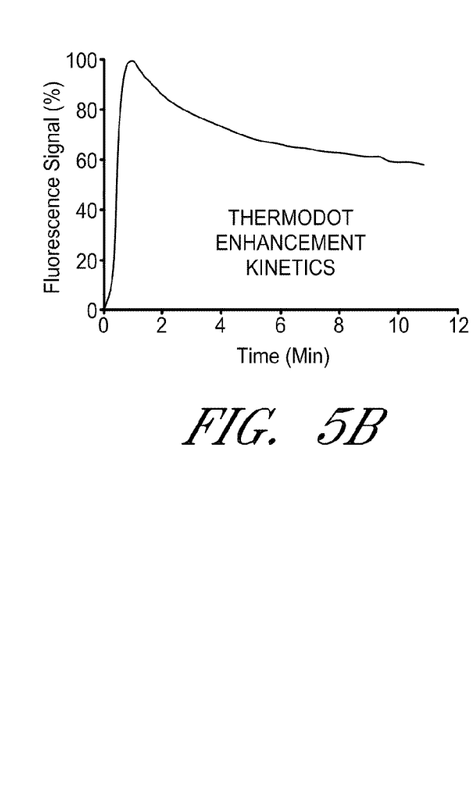
FIG. 5(b) shows temperature-sensitive contrast agents accumulated in the tumor very quickly (~1 min) and rapidly cleared out by liver.
Figure 5C:
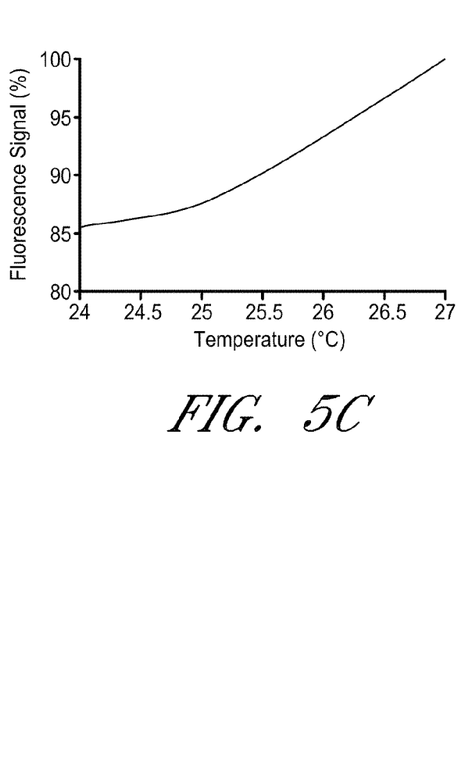
FIG. 5(c) shows when the animal is heated using an infrared heated lamp, the measured signal increased with the temperature. This particular temperature-sensitive contrast agent was optimized for a 25-28° C. range. Other versions of agents can be optimized for higher temperatures, e.g., a 30-35° C. range.

A temperature-sensitive contrast agent was tail-vein injected into a rat bearing R3220 AC breast cancer tumor model, with the fluorescent image shown in FIG. 5(a). The temperature-sensitive contrast agents accumulated in the tumor very quickly (~1 min) and rapidly cleared out by liver, FIG. 5(b). When the animal is heated using an infrared heated lamp, the measured signal increased with the temperature as shown in FIG. 5(c). This particular temperature-sensitive contrast agent was optimized for a 25-28° C. range. Other versions of agents can be optimized for higher temperatures, e.g., a 30-35° C. range.

The TM-FT system and method is particularly sensitive to fluorescence contrast and therefore likely more sensitive than photo-acoustic tomography (PAT). Besides obtaining fluorescence images at focused ultrasound resolution, the TM-FT can also render quantitatively accurate images using a proper reconstruction algorithm. This can either simple be done by guiding conventional FT reconstruction using TM-FT raw images as structural priori, or using a dedicated reconstruction algorithm described above [0029]. Finally, the technique described in this application is suitable for any temperature-sensitive agent that works in fluorescence mode and compatible to any other form of radiation that modulates the temperature of the medium.

REFERENCES (HEREIN INCORPORATED BY REFERENCE THERETO)

[1] Hsin-I Wu Lihong V. Wang *Biomedical Optics: Principles and Imaging*, 1 ed. (Wiley-Interscience, New Jersey, 2007).
[2] Frederic Leblond, Scott C. Davis, Pablo A. Valdés, and Brian W. Pogue, Journal of Photochemistry and Photobiology B: Biology 98 (1), 77 (2010).
[3] Masaki Kobayashi, Takashi Mizumoto, Yukihiro Shibuya, Masaru Enomoto, and Motohiro Takeda, Applied Physics Letters 89 (18), 181102 (2006).
[4] Baohong Yuan, Yuan Liu, Patrick M. Mehl, and Joseph Vignola, Applied Physics Letters 95 (18), 181113 (2009).
[5] C. Schutt, Proc. SPIE 8165 (1), 81650B (2011).
[6] B. Yuan, J. Biomed. Opt. 14 (2), 024043 (2009).
[7] Alexander L. Klibanov, Bioconjugate Chemistry 16 (1), 9 (2004).
[8] Amol M. Takalkar, Alexander L. Klibanov, Joshua J. Rychak, Jonathan R. Lindner, and Klaus Ley, Journal of Controlled Release 96 (3), 473 (2004).
[9] Chen Yongping and Li Xingde, *Biomedical Optics*, OSA Technical Digest, JMA105 (2010).
[10] Tae Kim, Yongping Chen, Christopher Mount, Wayne Gombotz, Xingde Li, and Suzie Pun, Pharmaceutical Research 27 (9), 1900 (2010).
[11] Scott C. Davis, Brian W. Pogue, Roger Springett, Christoph Leussler, Peter Mazurkewitz, Stephen B. Tuttle, Summer L. Gibbs-Strauss, Shudong S. Jiang, Hamid Dehghani, and Keith D. Paulsen, Review of Scientific Instruments 79 (6), 064302 (2008).
[12] Dax Kepshire, Niculae Mincu, Michael Hutchins, Josiah Gruber, Hamid Dehghani, Justin Hypnarowski, Frederic Leblond, Mario Khayat, and Brian W. Pogue, Review of Scientific Instruments 80 (4), 043701 (2009).
[13] Angelique Ale, Ralf B. Schulz, Athanasios Sarantopoulos, and Vasilis Ntziachristos, Medical Physics 37 (5), 1976 (2010).
[14] Yuting Lin, William C. Barber, Jan S. Iwanczyk, Werner W. Roeck, Orhan Nalcioglu, and Gultekin Gulsen, Journal of Biomedical Optics 15 (4), 040503 (2010).
[15] Yuting Lin, William C. Barber, Jan S. Iwanczyk, Werner Roeck, Orhan Nalcioglu, and Gultekin Gulsen, Opt. Express 18 (8), 7835 (2010).
[16] D. Gruber Josiah, Paliwal Akshat, Ghadyani Hamid, Maytin Edward, Hasan Tayyaba, and Pogue Brian, *Biomedical Optics*, OSA Technical Digest, BMB5 (2010).
[17] Minghua Xu and Lihong V. Wang, Review of Scientific Instruments 77 (4), 041101 (2006).
[18] Lihong V. Wang, Medical Physics 35 (12), 5758 (2008).
[19] Li Meng-Lin, Oh Jung-Taek, Xie Xueyi, Ku Geng, Wang Wei, Li Chun, G. Lungu, G. Stoica, and L. V. Wang, Proceedings of the IEEE 96 (3), 481 (2008).
[20] Daniel Razansky, Martin Distel, Claudio Vinegoni, Rui Ma, Norbert Perrimon, Reinhard W. Koster, and Vasilis Ntziachristos, Nat Photon 3 (7), 412 (2009).
[21] Rui Ma, Adrian Taruttis, Vasilis Ntziachristos, and Daniel Razansky, Opt. Express 17 (24), 21414 (2009).

What is claimed is:
1. An imaging system, comprising:
an excitation light source configured to generate excitation light;
an optical reporter and an associated nanoparticle or nanocapsule, the optical reporter configured to absorb excitation light and emit an optical signal;
a temperature-modulating energy source different from the excitation light source, the temperature-modulating energy source configured to provide temperature-modulating energy to the nanoparticle or nanocapsule, wherein the nanoparticle or nanocapsule is configured to absorb the temperature-modulating energy and generate heat to modulate the temperature of the nanoparticle or nanocapsule associated optical reporter, thereby modulating the intensity and/or lifetime of the optical signal; and a detector configured to detect the optical signal after temperature modulation of the nanoparticle or nanocapsule associated optical reporter.

2. The imaging system of claim 1, wherein the excitation light source is selected from a laser, a light emitting diode, and a UV light.

3. The imaging system of claim 1, wherein the nanoparticle or nanocapsule associated optical reporter comprises a temperature-sensitive fluorescence contrast agent.

4. The imaging system of claim 3, wherein the temperature-sensitive fluorescence contrast agent comprises ICG associated with the nanoparticle or nanocapsule.

5. The imaging system of claim 1, wherein the temperature-modulating energy source is configured to deliver high intensity focused ultrasound energy to the nanoparticle or nanocapsule associated optical reporter.

6. The imaging system of claim 1, wherein the temperature-modulating energy source is configured to deliver microwave energy to the nanoparticle or nanocapsule associated optical reporter.

7. The imaging system of claim 1, wherein the temperature-modulating energy source is configured to deliver radio frequency energy to the nanoparticle or nanocapsule associated optical reporter.

8. The imaging system of claim 1, wherein the temperature-modulating energy source is configured to deliver near-infrared energy to the nanoparticle or nanocapsule associated optical reporter.

9. The imaging system of claim 1, wherein the excitation light source and temperature-modulating energy source are located in different locations.

10. A temperature-modulated tomography method, comprising:
    administering an optical reporter and an associated nanoparticle or nanocapsule to a site for imaging, wherein the nanoparticle or nanocapsule associated optical reporter is configured to absorb excitation light and emit an optical signal;
    irradiating the site with excitation light from a first energy source;
    delivering sufficient temperature-modulating energy to the site so that the nanoparticle or nanocapsule absorbs the temperature-modulating energy and produces heat to modulate the temperature of the nanoparticle or nanocapsule associated optical reporter, the temperature-modulating from a second energy source different from the first energy source, thereby modulating the intensity and/or lifetime of the optical signal; and
    detecting the optical signal emitted by the nanoparticle or nanocapsule associated optical reporter.

11. The temperature-modulated tomography method of claim 10, wherein the nanoparticle or nanocapsule associated optical reporter comprises a temperature-sensitive fluorescence contrast agent.

12. The temperature-modulated tomography method of claim 11, wherein the temperature-sensitive fluorescence contrast agent comprises ICG associated with the nanoparticle or nanocapsule.

13. The temperature-modulated tomography method of claim 10, wherein the temperature-modulating energy is high intensity focused ultrasound energy.

14. The temperature-modulated tomography method of claim 10, wherein the temperature-modulating energy is microwave energy.

15. The temperature-modulated tomography method of claim 10, wherein the temperature-modulating energy is radio frequency energy.

16. The temperature-modulated tomography method of claim 10, wherein the temperature-modulating energy is near-infrared energy.

17. The temperature-modulated tomography method of claim 11, wherein a fluorescence intensity and/or a fluorescence lifetime of the optical signal is determined.

18. The temperature-modulated tomography method of claim 10, further comprising rendering a quantitatively accurate image using a reconstruction algorithm.

19. The imaging system of claim 1, wherein modulating the intensity and/or lifetime of the optical signal of the nanoparticle or nanocapsule associated optical reporter is reversible.

20. The temperature-modulated tomography method of claim 10, wherein modulating the intensity and/or lifetime of the optical signal of the nanoparticle or nanocapsule associated optical reporter is reversible.

* * * * *